US00PP08722P

United States Patent [19]

Bailey

[11] Patent Number: Plant 8,722

[45] Date of Patent: May 10, 1994

[54] COMPACT SHRUB DOGWOOD—BAILHALO CULTIVAR

[75] Inventor: Rodney P. Bailey, St. Paul, Minn.

[73] Assignee: Bailey Nurseries, Inc., St. Paul, Minn.

[21] Appl. No.: 998,242

[22] Filed: Dec. 8, 1992

[51] Int. Cl.[5] ..... A01H 5/00

[52] U.S. Cl. ..... Plt./53.2

[58] Field of Search ..... Plt. 53.2, 51.1, 54.1

*Primary Examiner*—James R. Feyrer
*Assistant Examiner*—Elizabeth C. Kemmerer
*Attorney, Agent, or Firm*—Burns, Doane, Swecker & Mathis

[57] ABSTRACT

A new and distinctive cultivar of shrub dogwood, botanically known as *Cornus alba* is provided. The new cultivar originated as a whole-plant mutation of unknown causation of the Argenteo-Marginata cultivar. A compact slower growing habit is exhibited in combination with the same attractive variegated green irregularly edged with white foliage of its parent which is well retained during the summer. Also, the branches of the new cultivar are finer textured, brighter, and darker in appearance than those of the parent. Other characteristics of the new cultivar are believed to be substantially identical to those of the parent cultivar. Plants of the new cultivar can be used to advantage as an attractive ornamental shrub for growing in smaller areas than its parent.

6 Drawing Sheets

SUMMARY OF THE INVENTION

The new cultivar was discovered during 1983 while growing in a production field of the Argenteo-Marginata cultivar (non-patented in the United States) of *Cornus alba* located near St. Paul, Minn. The Argenteo-Marginata cultivar of variegated shrub dogwood is believed to trace its origin to Europe. I was attracted to a single plant of the new cultivar because of its distinctive appearance. The new cultivar is believed to be a whole plant mutation of unknown causation. Had I not discovered and preserved this new cultivar it would have been lost to mankind. Softwood cuttings were propagated from the original plant during the summer of 1983, and the original plant was placed into a scion block during the spring of 1984.

It was found that the following combination of characteristics is exhibited by the new cultivar of *Cornus alba:*

(a) exhibits a full and rounded growth habit,
(b) exhibits a more compact growth habit than the Argenteo-Marginata cultivar with lesser internode lengths,
(c) is slower growing than the Argenteo-Marginata cultivar,
(d) exhibits a finer branching habit and brighter and darker red-brown bark than the Argenteo-Marginata cultivar,
(e) exhibits the same attractive variegated green irregularly edged with white foliage as the Argenteo-Marginata cultivar which is well retained during the summer, and
(f) is well adapted for growing as an ornamental shrub in a smaller area than the Argenteo-Marginata cultivar.

The new cultivar has been continuously evaluated for its horticultural performance since the time of its initial discovery. The characteristics of the new cultivar have been found to be stably manifest in succeeding generations following asexual propagation by softwood cuttings, carried out near St. Paul, Minn., U.S.A. A distinctive new cultivar is provided which is well suited for use as an attractive planting in the landscape.

The new compact shrub dogwood of the present invention has been named the Bailhalo cultivar, and is being marketed by Bailey Nurseries, Inc. of St. Paul, Minn., U.S.A., under the Ivory Halo trademark.

BRIEF DESCRIPTION OF THE PHOTOGRAPHS

The accompanying photographs show plants and plant parts of the cultivar *Cornus alba* as depicted in color as true as is reasonably possible to make the same in color illustrations of this character. The plants were grown at or near St. Paul, Minn., U.S.A.

FIG. 1 illustrates during the summer the original plant of the new cultivar. Such plant was transplanted during 1990 to near the offices of Assignee where studies of its characteristics were continued. The full and rounded growth habit is apparent.

Figure 1:
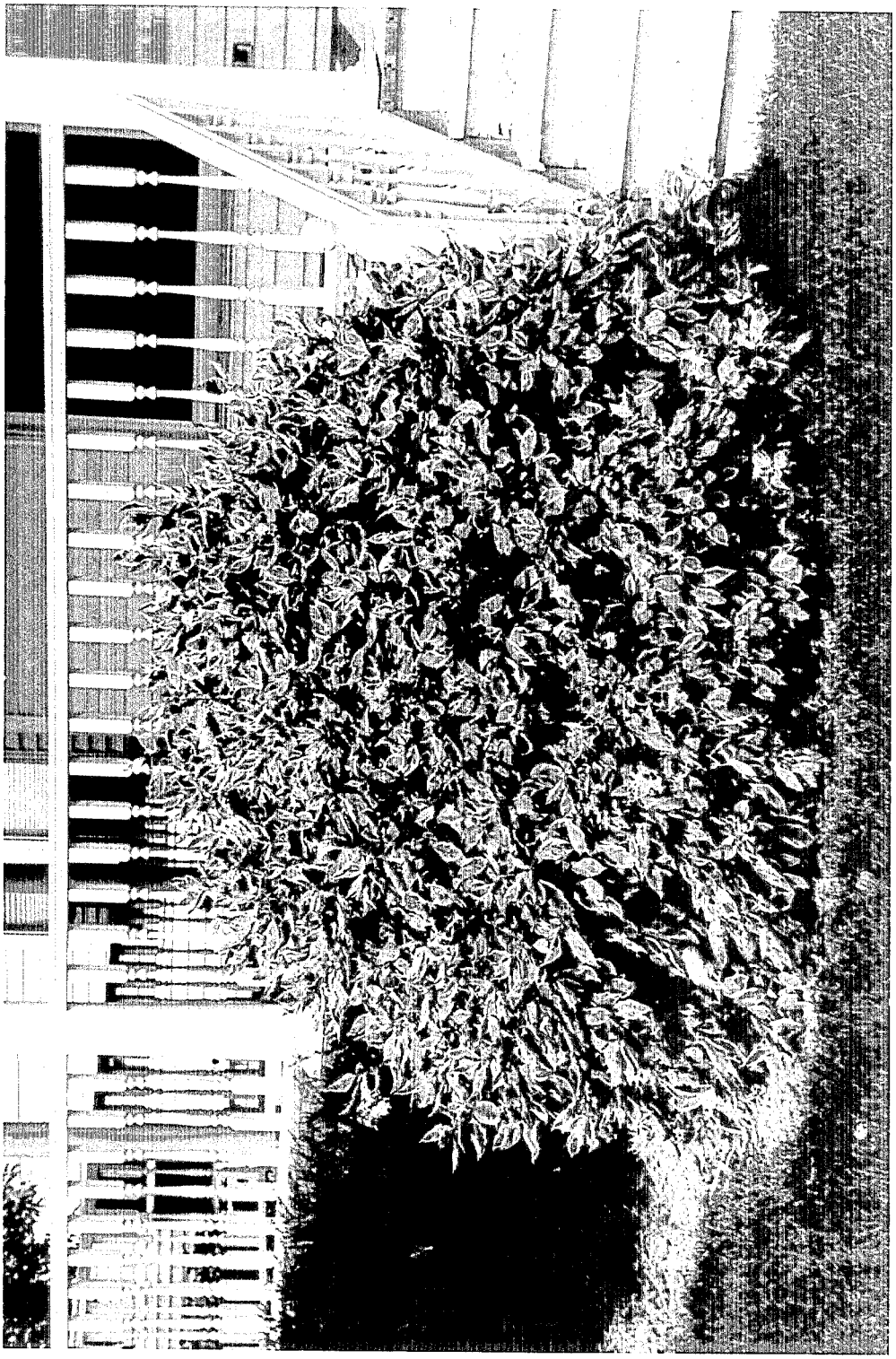
Figure 2:
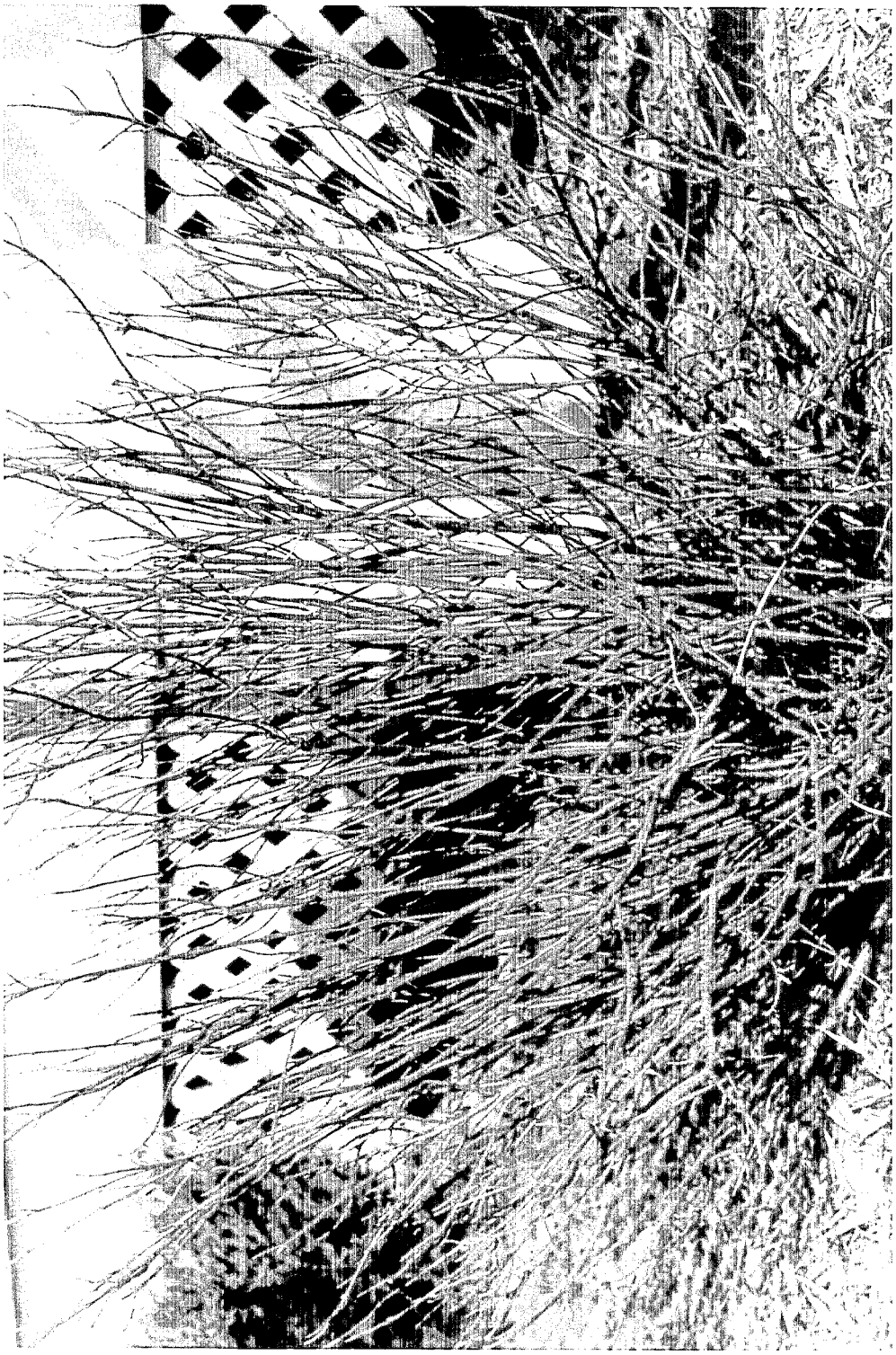
FIG. 2 illustrates during the winter the same original plant of the new cultivar as shown in FIG. 1. The attractive fine red-brown twigs are apparent.
Figure 3:
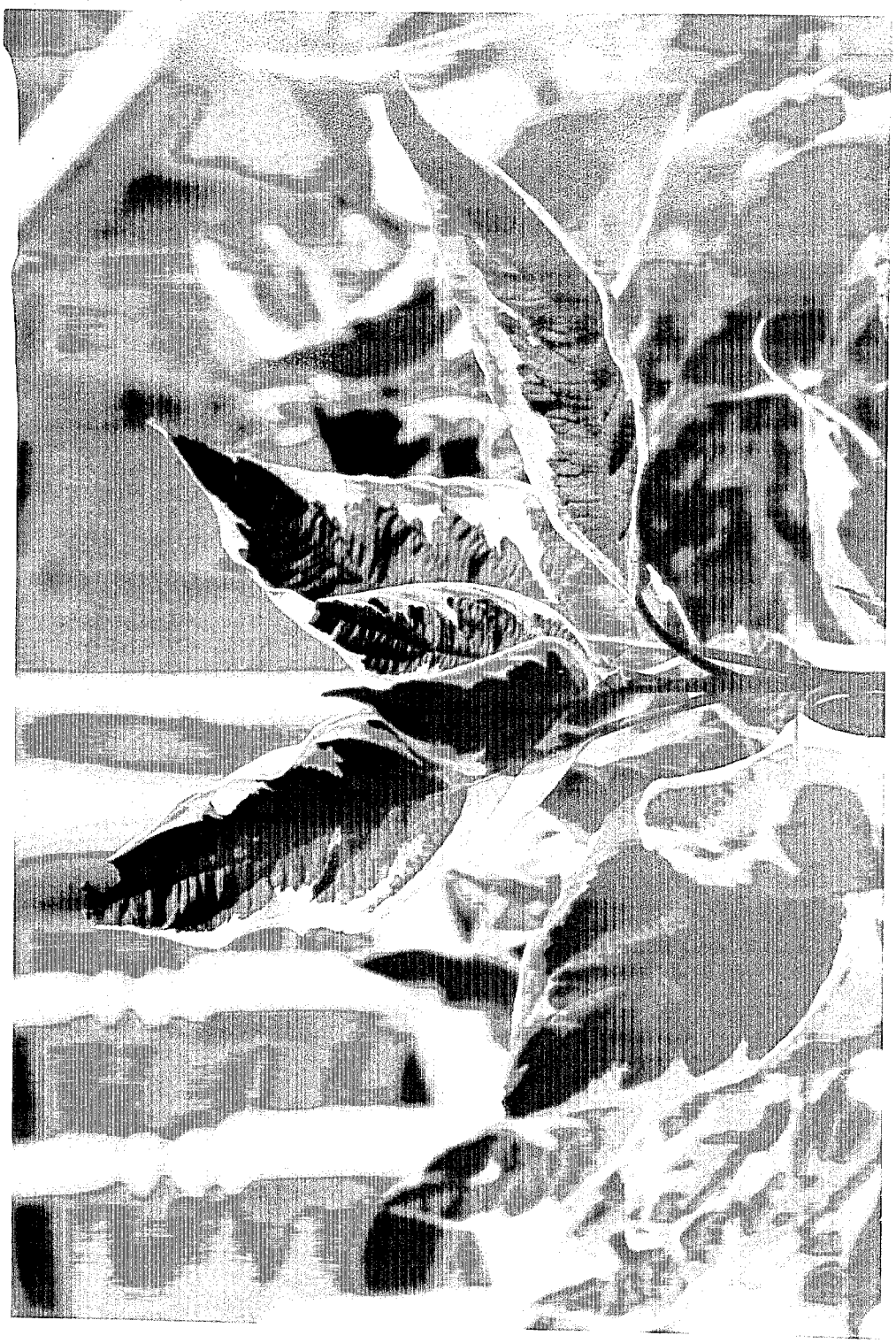
FIG. 3 illustrates the foliage during the summer of the original plant of the new cultivar. The attractive variegated green irregularly edged with white foliage is apparent.
Figure 4:
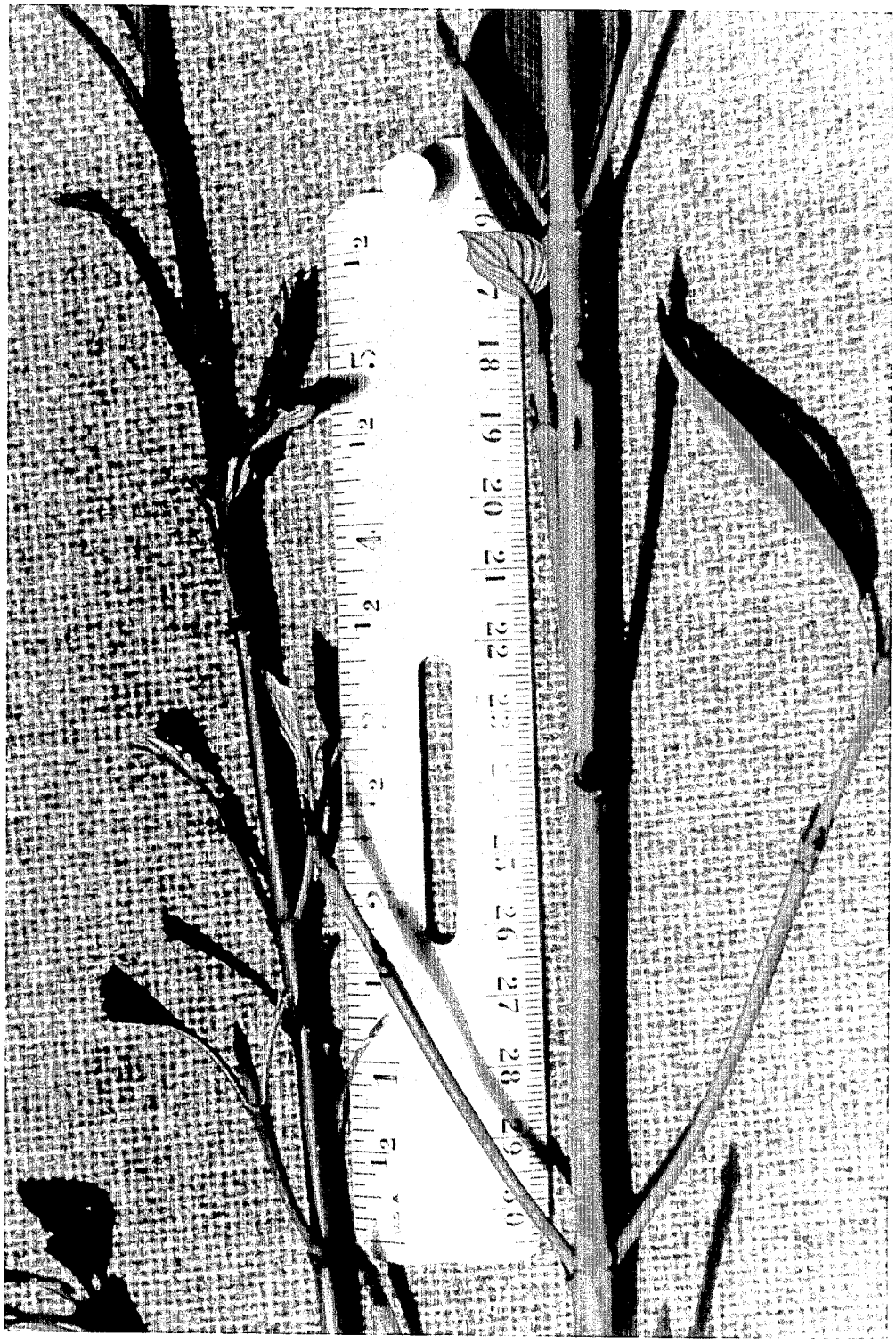

FIG. 4 illustrates for comparative purposes a typical branch of the new Bailhalo cultivar on the top and a typical branch of the parent Argenteo-Marginata cultivar on the bottom. The branches were obtained from two-year-old field grown plants. The photographs were obtained on Oct. 21, 1992. The lesser internode length exhibited by the new cultivar is apparent as is the brighter and darker bark coloration of the new cultivar.

Figure 5:
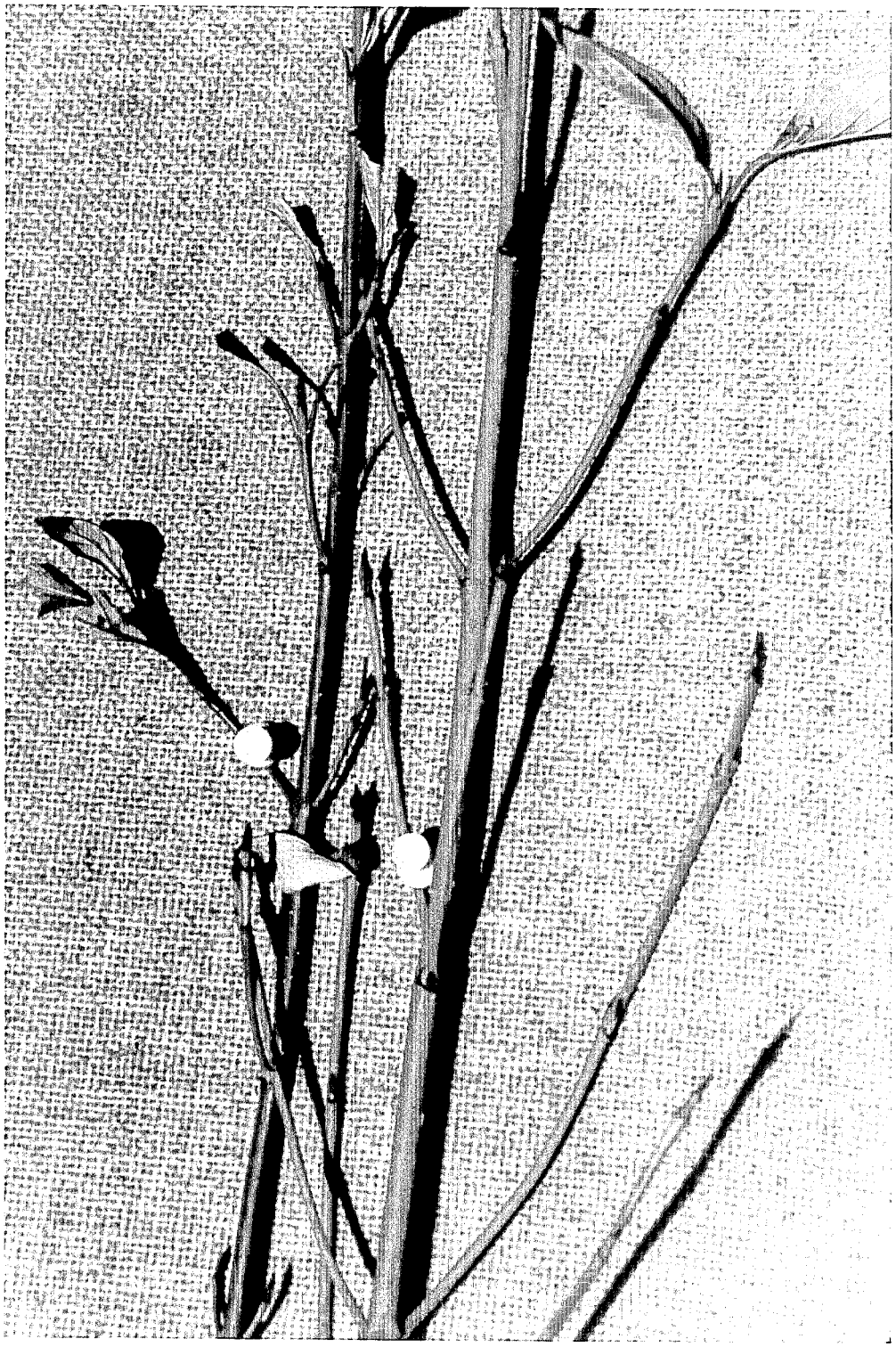

FIG. 5 illustrates for comparative purposes an additional typical branch of the new Bailhalo cultivar on the top and a typical branch of the parent Argenteo-Marginata cultivar on the bottom.

Figure 6:
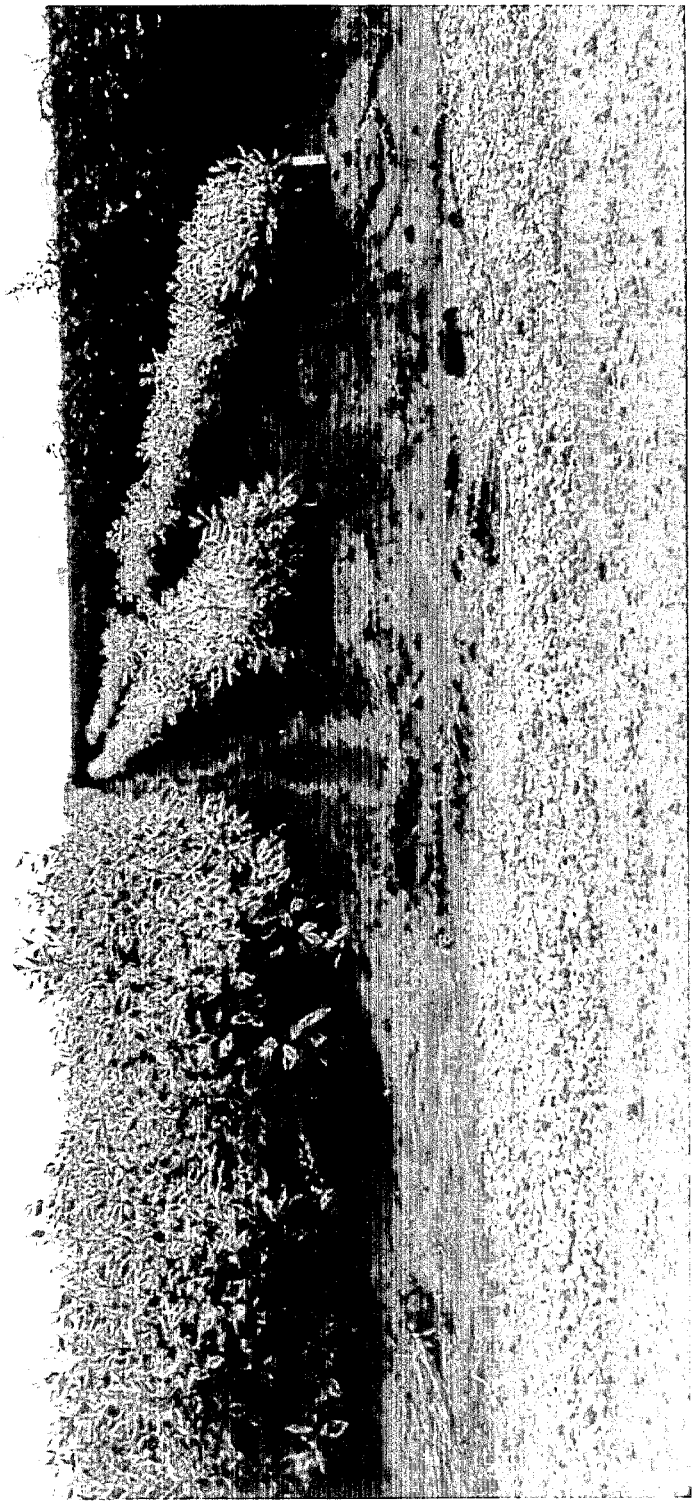

FIG. 6 illustrates for comparative purposes during mid-summer two rows of the new Bailhalo cultivar on the right and plants of the parent Argenteo-Marginata cultivar on the left. The plants were planted at the same time as rooted cuttings of comparable size. The plants illustrated were two years of age. The compact and slower growth habit of the new cultivar is readily apparent.

DETAILED DESCRIPTION OF THE NEW CULTIVAR

The following description of the new cultivar of *Cornus alba* is based upon the observation of the original plant being grown at or near St. Paul, Minn., U.S.A., as well as upon an observation of its progeny which were asexually reproduced by softwood cuttings and growing near the same location.

The new cultivar clearly exhibits a more compact growth habit, a reduced rate of growth, and a finer branching character than the parent Argenteo-Marginata cultivar. When typical internode lengths of two-year-old field grown plants were measured on Oct. 21, 1992, it was found that those of the new cultivar commonly measure approximately 1½ to 1¾ inches, while those of the new Argenteo-Marginata cultivar commonly measure approximately 2½ to 3 inches.

It additionally was observed on Oct. 21, 1992 that the bark of the new cultivar was brighter and darker than that of the Argenteo-Marginata cultivar. More specifically, the bark of the new cultivar was somewhat shiny (as illustrated) and generally corresponds to Greyed-Purple Group 185A of the R.H.S. Colour Chart of The Royal Horticultural Society, London, England. In contrast, the bark of the Argenteo-Marginata cultivar was duller in appearance (as illustrated) and generally corresponds to Greyed-Purple Group 185B.

The original nearly ten-year-old plant of the new cultivar is approximately 4½ feet in height and approximately 6 feet in width. While it is not possible at this time to specify with certainty the ultimate size that will be attained by the new cultivar, it is clear that its size for a given age during the first approximately ten years growth is considerably less than that of the parent Argenteo-Marginata cultivar. For instance, the parent cultivar at an age of ten years commonly will attain a height of approximately 6 to 10 feet, and a width of up to approximately 8 feet.

The other characteristics of the new cultivar are believed to be substantially identical to those of the parent Argenteo-Marginata cultivar. For instance, variegated green irregularly edged with white leaves of approximately the same size continue to be exhibited (as illustrated). As illustrated, the new variety exhibits attractive variegated green leaves irregularly edged with white as does its Argenteo-Marginata parent. When reference is made to the R.H.S. Colour Chart of The Royal Horticultural Society, the darker green of the leaves generally corresponds to Green Group 137B, the lighter green of the leaves generally corresponds to Greyed-Green Group 191A, and the white or cream of the leaves generally corresponds to Green-White Group 157D. Such leaves give the shrub a cool whitish appearance even on warm summer days. Also, there are no apparent differences in disease resistance, insect resistance, or adaptability to environmental conditions between the new cultivar and the Argenteo-Marginata cultivar.

The flowers of the new cultivar are believed to be identical to those of its Argenteo-Marginata cultivar. The flowers appear to be perfect, but are believed to be sterile since no seeds have been observed on either the Argenteo-Marginata cultivar or on the new cultivar when inspected under normal growing conditions. The reproductive organs of the new cultivar appear to be the same as those of the Argenteo-Marginata cultivar. Both the new cultivar and the Argenteo-Marginata cultivar do not form conspicuous bracts as are commonly formed on other species of Cornus.

The new cultivar is particularly suited for growing as an ornamental shrub which is attractive throughout the year with the red-brown twigs being visible in the winter and the variegated foliage being visible throughout much of the remainder of the year.

The new cultivar is believed to be suited for growing in Zones 3 to 7 of the United States Department of Agriculture Hardiness Map.

I claim:

1. A new and distinct cultivar of *Cornus alba* shrub, having the following combination of characteristics:

(a) exhibits a full and rounded growth habit,
(b) exhibits a more compact growth habit than the Argenteo-Marginata cultivar with lesser internode lengths,
(c) is slower growing than the Argenteo-Marginata cultivar,
(d) exhibits a finer branching habit and brighter and darker red-brown bark than the Argenteo-Marginata cultivar,
(e) exhibits the same attractive variegated green irregularly edged with white foliage as the Argenteo-Marginata cultivar which is well retained during the summer, and
(f) is well adapted for growing as an ornamental shrub in a smaller area than the Argenteo-Marginata cultivar;

substantially as illustrated and described.

* * * * *